(12) United States Patent
Drobyshev et al.

(10) Patent No.: US 11,401,219 B2
(45) Date of Patent: Aug. 2, 2022

(54) PROCESS FOR PRODUCING BUTADIENE FROM ETHANOL WITH IN SITU REGENERATION OF THE CATALYST OF THE SECOND REACTION STEP

(71) Applicants: IFP Energies nouvelles, Rueil-Malmaison (FR); COMPAGNIE GENERALE DES ETABLISSEMENTS MICHELIN, Clermont-Ferrand (FR)

(72) Inventors: Kirill Drobyshev, Rueil-Malmaison (FR); Rejane Dastillung, Rueil-Malmaison (FR); Jean-Christophe Gabelle, Rueil-Malmaison (FR); Matthieu Rolland, Rueil-Malmaison (FR)

(73) Assignees: IFP Energies nouvelles, Rueil-Malmaison (FR); COMPAGNIE GENERALE DES ETABLISSEMENTS MICHELIN, Clermont-Ferrand (DE)

( * ) Notice: Subject to any disclaimer, the term of this patent is extended or adjusted under 35 U.S.C. 154(b) by 0 days.

(21) Appl. No.: 17/415,806

(22) PCT Filed: Dec. 13, 2019

(86) PCT No.: PCT/EP2019/085114
§ 371 (c)(1),
(2) Date: Jun. 18, 2021

(87) PCT Pub. No.: WO2020/126921
PCT Pub. Date: Jun. 25, 2020

(65) Prior Publication Data
US 2022/0055969 A1    Feb. 24, 2022

(30) Foreign Application Priority Data

Dec. 21, 2018 (FR) .................................... 1873767

(51) Int. Cl.
*C07C 1/24* (2006.01)
*B01J 8/04* (2006.01)
(Continued)

(52) U.S. Cl.
CPC ...... *C07C 1/24* (2013.01); *B01J 8/04* (2013.01); *B01J 19/245* (2013.01);
(Continued)

(58) Field of Classification Search
CPC ...... C07C 1/24; C07C 45/002; C07C 2523/20; C07C 2523/72; C07C 2521/08;
(Continued)

(56) References Cited

U.S. PATENT DOCUMENTS 2,357,365 A * 9/1944 Van Horn et al. ........ B01J 38/12
                                                            208/47
2,915,570 A    12/1959 Busch-Petersen et al.
(Continued)

FOREIGN PATENT DOCUMENTS

FR    1294619 A    5/1962
FR    3026100 A1   3/2016
(Continued)

OTHER PUBLICATIONS

Burla, Jonathan; Fehnel, Ross; Louie, Philip; and Terpeluk, Peter, "Two-Step Production of 1,3-Butadiene From Ethanol" (2012). Senior Design Reports (CBE). 42. https://repository.upenn.edu/cbe_sdr/42 (Year: 2012).*
(Continued)

*Primary Examiner* — Ali Z Fadhel
(74) *Attorney, Agent, or Firm* — Millen White Zelano and Branigan, PC; Csaba Henter

(57) ABSTRACT

The present invention relates to a process for producing butadiene from ethanol, in two reaction steps, comprising a step a) of converting ethanol into acetaldehyde and a step b)
(Continued)

of conversion into butadiene, said step b) simultaneously implementing a reaction step and a regeneration step in (n+n/2) fixed-bed reactors, n being equal to 2 or a multiple thereof, comprising a catalyst, said regeneration step comprising four successive regeneration phases, said step b) also implementing a regeneration loop for the inert gas and at least one regeneration loop for the gas streams comprising oxygen.

20 Claims, 1 Drawing Sheet

(51) Int. Cl.
  *B01J 19/24* (2006.01)
  *B01J 23/20* (2006.01)
  *B01J 38/02* (2006.01)
  *B01J 38/04* (2006.01)
  *C07C 45/00* (2006.01)

(52) U.S. Cl.
  CPC ....... *B01J 19/2445* (2013.01); *B01J 19/2465* (2013.01); *B01J 23/20* (2013.01); *B01J 38/02* (2013.01); *B01J 38/04* (2013.01); *C07C 45/002* (2013.01); *B01J 2208/00548* (2013.01); *C07C 2523/20* (2013.01)

(58) Field of Classification Search
  CPC ..... C07C 1/2072; C07C 47/06; C07C 11/167; B01J 8/04; B01J 19/2445; B01J 19/245; B01J 19/2465; B01J 23/20; B01J 38/02; B01J 38/04; B01J 2208/00548; B01J 23/72; B01J 23/92; B01J 23/94; B01J 38/12; B01J 38/24; Y02P 20/584
  See application file for complete search history.

(56) References Cited

U.S. PATENT DOCUMENTS

| | | | |
|---|---|---|---|
| 9,950,969 | B2 | 4/2018 | Dastillung et al. |
| 10,358,396 | B2 | 7/2019 | Dastillung et al. |
| 2016/0145171 | A1* | 5/2016 | Spannhoff ............ C01B 39/085 585/327 |
| 2017/0349503 | A1* | 12/2017 | Chinta ................. C07C 1/2076 |
| 2018/0001304 | A1* | 1/2018 | Nishino ................... B01J 37/04 |
| 2018/0208522 | A1 | 7/2018 | Cadran et al. |
| 2018/0222813 | A1* | 8/2018 | Dagle ....................... C07C 1/20 |
| 2020/0317589 | A1* | 10/2020 | Sushkevich .............. B01J 29/74 |
| 2021/0214622 | A1 | 7/2021 | Engelman et al. |

FOREIGN PATENT DOCUMENTS

| | | |
|---|---|---|
| FR | 3026101 A1 | 3/2016 |
| FR | 3038851 A1 | 1/2017 |
| WO | 17091771 A2 | 6/2017 |

OTHER PUBLICATIONS

International Search Report PCT/EP2019/085114 dated Mar. 16, 2020 (pp. 1-2).

* cited by examiner

PROCESS FOR PRODUCING BUTADIENE FROM ETHANOL WITH IN SITU REGENERATION OF THE CATALYST OF THE SECOND REACTION STEP

TECHNICAL FIELD

The invention relates to a process for producing butadiene from ethanol operating in two reaction steps, a first step of converting ethanol into acetaldehyde and a second step of converting a mixture of ethanol and acetaldehyde into, this second step being performed in several reactors functioning in parallel, in the presence of a catalyst regenerated in situ.

PRIOR ART

Processes for producing butadiene from ethanol were developed in particular by the Russians on the basis of the studies by Lebedev in the 1920s (one-step reaction process) and by the Americans during the Second World War from the studies by Ostromilenski (two-step reaction process: dehydrogenation of ethanol to acetaldehyde, then production of butadiene from an ethanol/acetaldehyde mixture). This two-step process affords slightly better yields. It was performed during the 1940s in the United States. All the units of this type were shut down for mainly economic reasons.

Processes for producing butadiene from ethanol, in the Lebedev version (one step) or the Ostromilenski version (two steps), have a conversion per step of less than 50%.

Another problem of the process is the production of a wide variety of impurities of all kinds: saturated, unsaturated and aromatic hydrocarbons, but also oxygenated products such as alcohols, phenols, aldehydes, ketones, acids, esters, ethers or acetals.

The reason for this is that the overall reaction for the transformation of ethanol into butadiene hides numerous chemical reactions comprising a dehydrogenation reaction for generating acetaldehyde (I), an aldolization/crotonization reaction of acetaldehyde to crotonaldehyde (II), a Merwein-Pondorff-Verley (MPV) reaction between ethanol and crotonaldehyde (III) and finally a step of dehydration of crotyl alcohol to butadiene (IV).

I: $CH_3CH_2OH=CH_3CHO+H_2$
II: $2\ CH_3CHO=CH_3CHCH-CHO+H_2O$
III: 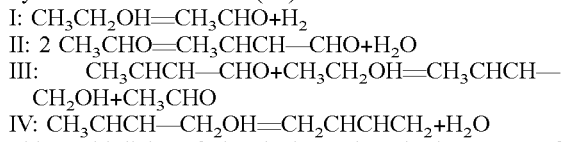$+CH_3CH_2OH=CH_3CHCH-CH_2OH+CH_3CHO$
IV: $CH_3CHCH-CH_2OH=CH_2CHCHCH_2+H_2O$ This multiplicity of chemical reactions is the source of numerous byproducts if the sequence of steps is not performed in the order stated above, notably with the presence of secondary dehydration and condensation reactions. Furthermore, other reactions may take place (such as isomerization, cyclization, Diels-Alder reaction, etc.), further increasing the number of byproducts.

Even if many of the byproducts are entrained with the reaction effluent toward separation/processing units downstream of the reactors, as in the CARBIDE process for the two-step production of 1,3-butadiene, presented in particular in the book "Synthetic Rubber", chapter 4 (W. J. Toussaint and J. Lee Marah), or more recently in the processes of the patents FR 3 026 100 and FR 3 026 101, the catalyst, in particular used during the second step for the conversion of the ethanol-acetaldehyde mixture into 1,3-butadiene, undergoes a rapid reduction in its activity, notably within a few weeks, or even a few days.

Many recent studies have focused on improving the overall butadiene yield of the process, for instance the studies described in the French patent FR 3 026 100, or on improving the activity and selectivity of the catalysts for the second reaction step (cf. for example FR 3 038 851). More particularly, patent FR 3 026 100 describes a two-step process for producing butadiene from an ethanol feedstock obtained from renewable sources, which makes it possible to remove the impurities while at the same time minimizing the loss of ethanol and acetaldehyde and thus maximizing the overall yield of the process. The process described also makes it possible to limit the consumption of utilities, thus reducing the energy consumption of the process. However, patent FR 3 026 100 is silent as regards a system for regenerating the catalyst notably used in the second reaction step.

There are few, if any, studies relating to the regeneration of catalysts for conversion of the ethanol/acetaldehyde mixture into butadiene. It thus appears essential to develop a method for regenerating the catalysts in particular for the second reaction step for conversion of ethanol into butadiene, while at the same time maximizing the butadiene yield.

Patent FR 1 294 619 describes a process for the simultaneous regeneration of a catalyst for a cyclic dehydrogenation system with multiple fixed-bed reactors, the catalyst being regenerated under a stream of air and in the presence of a combustible gas such as natural gas (or an equivalent gas composed of $C_1$-$C_4$ hydrocarbons), without recycling of the regeneration gas. U.S. Pat. No. 2,357,365 describes a conversion-regeneration process in a multi-reactor system, the reactors functioning in pairs, one being in the operational phase while the second is undergoing regeneration. The regeneration of the catalyst is operated simultaneously in at least two reactors, under a gas stream composed of nitrogen and oxygen in a content of 1-2 mol %, said gas stream circulating in a regeneration loop.

U.S. Pat. No. 2,915,570 describes the regeneration of a catalyst for the conversion of hydrocarbons into butadiene, under a stream of air at at least 540° C., said catalyst being based on chromium on an alumina support.

One of the constraints of the process for converting ethanol into butadiene in two reaction steps is the complexity of the protocol for regeneration in particular of the catalysts for the second step. Specifically, the regeneration protocol, which is well known to those skilled in the art, comprises a sequence of phases of flushing under a stream of inert gas with various oxygen contents. This sequence of phases of flushing different compositions with gas streams becomes a problem that is all the more difficult to solve the shorter the duration of the catalytic cycle of the catalysts, in particular based on tantalum, used for the second step.

The present invention is directed toward solving these regeneration problems without having an impact on the butadiene productivity. More particularly, the present invention is directed toward proposing a process for producing butadiene, in two reaction steps, comprising an optimized method for the in situ regeneration of the catalyst for the second reaction step, said process making it possible to ensure the continuous production of butadiene in a maximized yield and to reduce the fluctuations of the composition leaving the reactors and thus of the flow rate of butadiene produced.

SUMMARY OF THE INVENTION

The invention relates to a process for producing butadiene from ethanol, comprising at least the following steps:

a) a step of converting ethanol into acetaldehyde, to produce an ethanol/acetaldehyde effluent, comprising at least one reaction section (A) fed with a stream comprising ethanol and operated in the presence of a catalyst (Ca);

b) a butadiene conversion step comprising at least one reaction-regenerative section in which are simultaneously performed a reaction step and a regeneration step in (n+n/2) fixed-bed reactors, n being an integer equal to 2 or a multiple thereof, said (n+n/2) fixed-bed reactors each comprising at least one fixed bed of a catalyst (Cb), said (n+n/2) fixed-bed reactors functioning in parallel and in sequence so that said reaction step starts in each of said reactors with a time shift equal to half of the catalytic cycle time of said catalyst (Cb), said reaction-regenerative section comprising a regeneration loop for inert gas and at least one regeneration loop for a gas stream comprising oxygen, and so that, at each instant:

b1) said reaction step is operated in n of said fixed-bed reactors, n being an integer equal to 2 or a multiple thereof, fed at least with a fraction of said ethanol/acetaldehyde effluent obtained from step a), at a temperature of between 300 and 400° C., at a pressure of between 0.1 and 1.0 MPa, for a time equal to the catalytic cycle time of said catalyst (Cb), to produce a reaction effluent, and b2) said regeneration step is operated, in n/2 of said fixed-bed reactors, for a total time equal to half of the catalytic cycle time of said catalyst (Cb), and comprises the following four successive phases:

i. a stripping phase operated at a temperature of between 300 and 400° C., under a stream of inert gas, said phase i) starting on conclusion of the reaction step b1); and then ii. a first combustion phase operated on conclusion of phase i) under a gas stream comprising said inert gas and oxygen in a content of less than or equal to 1 vol % relative to the total volume of said gas stream, at a temperature of between 300 and 450° C.; and then iii. a second combustion phase operated on conclusion of the first combustion phase ii) under a gas stream comprising said inert gas and oxygen in a content of greater than or equal to 2 vol % relative to the total volume of said gas stream, at a temperature of between 390 and 550° C.; and then iv. a final stripping phase operated at a temperature of between 550° C. and 300° C., under a stream of said inert gas.

The process according to the invention, which uses the two-step route for converting ethanol into butadiene, allows the in situ regeneration of the catalyst for the second conversion step. One of the advantages of this in situ regeneration lies in the fact that it can at least partly compensate for the problem of rapid fouling of the catalyst for the second step. The regeneration of the process according to the invention follows relatively mild operating conditions for removing the coke deposited on the catalyst, thus avoiding premature degradation of the catalyst while at the same time allowing very good regeneration performance, i.e. while permitting efficient combustion of the coke deposited on the catalyst for the second reaction step.

One of the advantages of the process according to the invention lies in the fact that it can ensure the continuous production of butadiene, and does so with limited fluctuations of the composition of the effluent produced and thus low variations of the flow rate of butadiene produced. Specifically, since it uses a multi-reactor system in particular for the second conversion step, with reactors functioning in parallel, and allows rapid passage in a reactor from the operational mode to the regeneration mode, and conversely from the regeneration mode to the operational mode, the process according to the invention ensures a constant flow rate of the effluent at the outlet of the reaction units and homogenizes the composition of the effluent produced throughout the production. Under the conditions of the process according to the invention, the production of butadiene is ensured continuously.

Although it comprises a continuous reaction-regeneration system, the process according to the invention which includes at least two regeneration loops also affords a substantial saving in utilities. It makes it possible notably to limit the consumption of inert gas, such as nitrogen, which is at least partly recycled. The process according to the invention also allows economic optimization of the process for producing butadiene from ethanol in two reaction steps. The process of the present invention may, very advantageously, be integrated into a complex process for converting ethanol into butadiene, comprising one or more separation and/or purification units, making it possible to produce a very pure butadiene and to recover the unconverted or partially converted reagents and to recycle them into the reactors. Such a process is very well described, for example, in French patent FR 3 026 100.

DESCRIPTION OF THE EMBODIMENTS

According to the present invention, the term "multi-reactor system" or "multiple-reactor system" means a set of (n+n/2) fixed-bed reactors, n being an integer equal to 2 or a multiple thereof, or a set of at least three (i.e. 2+1) reactors, functioning in parallel and sequentially, i.e. such that the reaction step, notably reaction step b1), starts in each of the reactors of said multi-reactor system with a time shift relative to each other. Preferably, the multi-reactor system of step b) of the process of the invention comprises three fixed-bed reactors, i.e. the integer n is equal to 2. In practice, in the case where the multi-reactor system of step b) of the process according to the invention comprises three reactors (R1, R2 and R3), the reaction step b1) starts first in reactor R1, then in reactor R2 after a certain time, noted as t, then in R3 after the same time t relative to R2. Since the reaction step b1) and the regenerative step b2) follow each other successively and cyclically in each reactor, the regeneration also starts in sequence in each of the reactors. However, at a given moment, since the reactors function in parallel, the reaction and regeneration steps are simultaneous in the multi-reactor system containing (n+n/2) reactors.

According to the present invention, the fixed-bed reactors are said to be "non-operational" or "in non-operational mode" as soon as the regeneration step b2) starts and up to the end of said regeneration step, in particular up to the end of the final stripping phase iv). Conversely, the fixed-bed reactors are said to be "operational" or "in operational mode" when the reactions for conversion of the ethanol/acetaldehyde mixture into butadiene are performed in said fixed-bed reactors, i.e. as soon as the reaction step b1) starts up to the end of the catalytic cycle of the catalyst (Cb) in said fixed-bed reactors. Very advantageously, during step b) of conversion into butadiene of the process of the invention, there are simultaneously n fixed-bed reactors in operational mode and n/2 fixed-bed reactors in non-operational mode.

According to the present invention, the term "loop regeneration" means that the regeneration gases of step b2) of the process of the invention are at least partly treated, purified and recycled. Thus, the regeneration step b2) uses at least two regeneration loops for the regeneration gases. Preferably, the regeneration step b2) comprises a regeneration loop for the inert gas and at least one regeneration loop for the gas streams comprising oxygen. Each regeneration loop preferably comprises a system for treating and purifying the corresponding gas stream. Each regeneration loop may independently comprise a purge for removing any waste, notably organic compounds resulting from the combustion of coke.

According to the invention, the term "catalytic cycle" of a catalyst, in particular of (Cb) of the second reaction step, means the operational phase of said catalyst during which said catalyst fully serves its purpose in the reaction notably for conversion of the ethanol/acetaldehyde mixture into butadiene. Preferably, the catalytic cycle of the catalyst (Cb) corresponds to the operational phase of said catalyst when a minimum of 16 mol %, preferably of 23 mol %, of conversion of ethanol per step on said catalyst (Cb) of the second reaction step (i.e. reaction step b1) of the process according to the invention) is ensured.

According to the present invention, when the temperature is said to be "constant", it is clearly understood that it is the nominal temperature that is constant, the real temperature possibly oscillating around this nominal value.

Similarly, a temperature increase or decrease ramp means that the nominal temperature undergoes a temperature increase or decrease, the real temperatures oscillating around the nominal temperature.

According to the present invention, the expression "between . . . and . . . " means that the limit values of the interval are included in the described range of values. If such were not the case and if the limit values were not included in the range described, such a clarification will be given by the present invention.

Thus, the invention relates to a process for producing butadiene from ethanol, in two reaction steps, comprising a sequence of reaction and regeneration steps in a multiple-reactor system, the reactors functioning in parallel and in sequence.

More particularly, the invention relates to a process for producing butadiene from ethanol, comprising at least the following steps:

a) a step of converting ethanol into acetaldehyde, to produce an ethanol/acetaldehyde effluent, comprising at least one reaction section (A) fed with a stream comprising ethanol and operated in the presence of a catalyst (Ca); preferably, said step for converting ethanol into acetaldehyde is performed at a temperature of between 200 and 500° C., preferentially between 250° C. and 300° C., and at a pressure of between 0.1 and 1.0 MPa, preferentially between 0.1 and 0.5 MPa, more preferably between 0.1 and 0.3 MPa;

b) a butadiene conversion step comprising at least one reaction-regenerative section in which are simultaneously performed a reaction step and a regeneration step in (n+n/2) fixed-bed reactors, n being an integer equal to 2 or a multiple thereof, said (n+n/2) fixed-bed reactors each comprising at least one fixed bed of a catalyst (Cb), preferably based on tantalum, said (n+n/2) fixed-bed reactors functioning in parallel and in sequence so that said reaction step starts in each of said reactors with a time shift equal to half of the catalytic cycle time of said catalyst (Cb), said reaction-regenerative section comprising a regeneration loop for inert gas and at least one regeneration loop for a gas stream comprising oxygen, and so that, at each instant:

b1) said reaction step is operated in n of said fixed-bed reactors, n being an integer equal to 2 or a multiple thereof, fed at least with a fraction of said ethanol/acetaldehyde effluent obtained from step a), at a temperature of between 300 and 400° C., preferably between 300 and 360° C., at a pressure of between 0.1 and 1.0 MPa, preferably between 0.2 and 0.4 MPa, and for a time equal to the catalytic cycle time of said catalyst (Cb), to produce a reaction effluent, and b2) said regeneration step is operated, in n/2 of said fixed-bed reactors, which are advantageously non-operational, for a total time equal to half of the catalytic cycle time of said catalyst (Cb), and comprises, preferably consists of, the following four successive phases:

i. a stripping phase operated at a temperature of between 300 and 400° C., preferably between 330 and 370° C., under a stream of inert gas, preferably of nitrogen, of carbon dioxide ($CO_2$) or mixtures thereof, and very preferably under a stream of nitrogen, advantageously at a flow rate of between 0.5 and 1.5 $Nm^3$/h/kg of catalyst, preferably equal to 1 $Nm^3$/h/kg of catalyst, said phase i) starting on conclusion of the reaction step b1); and then ii. a first combustion phase operated on conclusion of phase i), under a gas stream comprising said inert gas and oxygen (in particular in the form of dioxygen $O_2$) in a content of less than or equal to 1 vol % relative to the total volume of said gas stream, preferably in a content of between 0.1 and 1 vol %, preferentially between 0.3 and 0.7 vol % relative to the total volume of said gas stream, at a temperature of between 300 and 450° C., preferably between 330 and 430° C., in particular at a constant temperature of between 330 and 370° C. followed by a temperature increase ramp of 10 to 30° C./h and then a phase at a constant temperature of between 390 and 430° C., and advantageously at a flow rate of said gas stream of between 3.5 and 5.0 $Nm^3$/h/kg of catalyst, preferably between 3.8 and 4.6 $Nm^3$/h/kg of catalyst; and then iii. a second combustion phase operated on conclusion of the first combustion phase ii), under a gas stream comprising said inert gas and oxygen (in particular in the form of dioxygen $O_2$) in a content of greater than or equal to 2 vol % relative to the total volume of said gas stream, preferably in a content of between 2 and 20 vol %, preferentially between 2 and 10 vol %, more preferentially between 4 and 8 vol % relative to the total volume of said gas stream, at a temperature of between 390 and 550° C., preferably at a constant temperature of between 390 and 430° C. followed by a temperature increase ramp of 10 to 30° C./h and then a phase at a constant temperature of between 460 and 510° C., and advantageously at a flow rate of said gas stream of between 2.5 and 3.5 $Nm^3$/h/kg of catalyst, preferably between 2.7 and 3.0 $Nm^3$/h/kg of catalyst; and then iv. a final stripping phase operated at a temperature of between 550 and 300° C., preferably on a temperature decrease ramp of 50 to 150° C./h followed by a phase at a constant temperature of between 300 and 400° C., preferably between 330 and 370° C., under a stream of said inert gas, preferably of nitrogen, of carbon dioxide ($CO_2$) or mixtures thereof, and very preferably under a stream of nitrogen, advantageously at a flow rate of between 0.5 and 1.5 $Nm^3$/h/kg of catalyst, preferably equal to 1 $Nm^3$/h/kg of catalyst.

Preferably, the process according to the invention comprises the succession, in particular in this order, of step a) of converting ethanol into acetaldehyde and of step b) of conversion into butadiene, without an intermediate step.

Very advantageously, the process according to the invention may be integrated into a more global process for converting ethanol into butadiene, in particular comprising separation and purification steps downstream of the conversion reactors, for example such as the process described in French patent FR 3 026 100.

The Feedstock

In accordance with the invention, the process converts ethanol into butadiene.

Advantageously, the stream comprising converted ethanol which feeds the process according to the invention comprises at least 80% by weight of ethanol, preferentially at least 90% by weight, and preferably at least 93% by weight. Very preferably, the ethanol feedstock comprising said stream meets the EN 15376 fuel ethanol specifications. Said ethanol feedstock may originate from any fossil, plant or animal origin, and in particular from processes for producing ethanol from plant resources.

Step a) of Converting Ethanol Into Acetaldehyde

In accordance with the invention, the process comprises a step a) of converting ethanol into acetaldehyde, to produce an ethanol/acetaldehyde effluent, advantageously in liquid form.

Said step a) of the process according to the invention comprises at least one reaction section (A) fed with a stream comprising ethanol.

Said step a) for converting ethanol into acetaldehyde is operated in the presence of a catalyst (Ca), advantageously of an alcohol dehydrogenation catalyst. Any catalyst, notably any catalyst for the dehydrogenation of alcohols, in particular of ethanol, known to those skilled in the art may be used in step a) of the process according to the invention. Very preferably, the catalyst (Ca) of said step a) of the process according to the invention is an ethanol dehydrogenation catalyst comprising a dehydrogenating element, more particularly a copper element, more preferentially a copper oxide or a mixture of chromium oxide and copper oxide, and a matrix in particular based on silica.

Advantageously, step a) of the process of the invention is operated under temperature and pressure conditions known to those skilled in the art. Preferably, the reaction section (A) of step a) of the process of the invention is operated at a temperature of between 200 and 500° C., preferentially between 250° C. and 300° C., and at a pressure of between 0.1 and 1.0 MPa, preferentially between 0.1 and 0.5 MPa, more preferably between 0.1 and 0.3 MPa.

Said step a) of the process according to the invention makes it possible advantageously to convert ethanol into acetaldehyde by dehydrogenation of ethanol. Preferably, the conversion of ethanol into acetaldehyde is between 25% and 40% per step, with a selectivity of between 85% and 100% toward acetaldehyde, preferably between 90% and 97% toward acetaldehyde. In addition to acetaldehyde, the dehydrogenation reaction that is performed during step a) of the process according to the invention produces hydrogen. Thus, preferably, step a) of the process of the invention also comprises a separation section for separating at least one hydrogen effluent in gaseous form and said ethanol/acetaldehyde effluent in liquid form. When it is integrated into said step a) of the process according to the invention, said optional separation section uses gas/liquid separation means known to those skilled in the art. Preferably, said separation section comprises a gas/liquid separator operated at a pressure of between 0.1 and 0.3 MPa and at a temperature of between 25 and 60° C.

Step b) of Conversion Into Butadiene

In accordance with the invention, step b) of conversion into butadiene of the process of the invention comprises at least one reaction-regenerative section in which a reaction step and a regeneration step are performed simultaneously. Said reaction-regenerative section comprises a multiple-reactor system comprising (n+n/2) fixed-bed reactors, n being an integer equal to 2 or a multiple thereof, n preferably being an integer equal to 2, said (n+n/2) fixed-bed reactors functioning in parallel and in sequence. Said reaction-regenerative section also comprises at least two regeneration loops and preferably a system of lines and of valves for circulating the regeneration gas streams in each of the (n+n/2) reactors of said reaction-regenerative section. More particularly, said reaction-regenerative section comprises a regeneration loop for the inert gas and at least one regeneration loop for the gas stream comprising oxygen.

If, at a given moment, said reaction step b1) and regenerative step b2) are performed simultaneously in said multiple-reactor system, i.e. in all of the (n+n/2) fixed-bed reactors of said reaction-regenerative section, they are performed successively and cyclically in each of said fixed-bed reactors.

In accordance with the invention, step b) is a step of converting an ethanol and acetaldehyde mixture into butadiene, said mixture comprising at least a fraction of said ethanol/acetaldehyde effluent obtained from step a).

According to the invention, each fixed-bed reactor comprises at least one fixed bed of a catalyst (Cb). Said catalyst (Cb) advantageously comprises an element selected from the group consisting of tantalum, zirconium and columbium (or niobium), preferably in their oxide form. Preferably, the catalyst (Cb) comprises the element tantalum, and preferably a tantalum oxide. Advantageously, the catalyst (Cb) also comprises a support, preferably a mesoporous matrix, preferably based on silica. For example, said catalyst (Cb) is the catalyst described in patent application FR 3 038 851. The catalytic cycle time of said catalyst (Cb) is in particular greater than or equal to 1 day, preferably greater than or equal to 6 days, and less than or equal to 20 days, more particularly less than or equal to 15 days. For example, the cycle time of the catalyst (Cb) of the process according to the invention is equal to 10 days. This time makes it possible to ensure an ethanol conversion per step on said catalyst (Cb) at least equal to 16 mol %, preferably at least equal to 23 mol %.

The functioning in sequence of said (n+n/2) reactors, i.e. the functioning time shift of said reactors, is adjusted so that the reaction step b1) starts in each of said reactors with a time shift equal to half of the catalytic cycle time of said catalyst (Cb), so that the reaction step b1) starts the reactor $R_{i+1}$ with a time shift equal to half of the catalytic cycle time of said catalyst (Cb) relative to the reactor $R_i$, with i being an integer ranging from 1 to ((n+n/2)−1). For example, in the case where the multi-reactor system comprises three reactors (2+1 reactors) and in which the catalytic cycle time is 10 days, the reaction step b1) starts, starts first in reactor R1, then in reactor R2 five days after having started in reactor R1, then in reactor R3 five days after having started in reactor R2.

In accordance with the invention, step b) comprises a reaction step b1) to produce a reaction effluent, advantageously comprising butadiene.

Advantageously, said fixed-bed reactors used in said reaction step b1) according to the invention, i.e. said operational reactors, are fed with at least a fraction of said ethanol/acetaldehyde effluent obtained from step a). Optionally, said operational fixed-bed reactors used in said reaction step b1) according to the invention may also be fed with a supply of ethanol, notably comprising a recycled ethanol stream, and/or a supply of acetaldehyde, notably comprising a recycled acetaldehyde stream, said recycled acetaldehyde and ethanol streams being obtained from purification-separation units that may be present downstream of the process according to the invention, and in which the unconverted reagents (ethanol, acetaldehyde) are advantageously separated. When said reaction step b1) according to the invention comprises an additional supply of ethanol and/or of acetaldehyde, said feed flow rates of said reaction step b1), in particular in said at least a fraction of said ethanol/acetaldehyde effluent obtained from step a) and in the optional supplies of ethanol and of acetaldehyde, are advantageously adjusted so that the mole ratio between the total molar amount of ethanol relative to the total molar amount of acetaldehyde at the inlet of the operational fixed-bed reactors of said reaction step b1) is between 1 and 5, preferably between 2 and 4 and very preferably between 2.4 and 3.6.

According to the invention, said reaction step b1) is performed in n of said fixed-bed reactors, n being an integer equal to 2 or a multiple thereof, functioning in parallel and in sequence. Advantageously, said reaction step b1) is operated at a temperature of between 300 and 400° C., preferably between 300 and 360° C., at a pressure of between 0.1 and 1.0 MPa, preferably between 0.2 and 0.4 MPa, and for a time equal to the catalytic cycle time of said catalyst (Cb). Preferably, said reaction step b1) is operated at an hourly space velocity (HSV) of between 0.8 and 2.5 $h^{-1}$, preferably between 0.8 and 2 $h^{-1}$, the hourly space velocity (HSV, weight per weight per hour) being defined as the ratio between the mass flow rate of ethanol/acetaldehyde feedstock entering the n operational reactors and the mass of catalyst included in said n operational reactors.

Advantageously, said reaction step b1) makes it possible to convert at least a portion of the ethanol/acetaldehyde mixture into butadiene. The butadiene selectivity of this reaction step is preferably greater than 60%, preferably greater than 70%, very preferably greater than 80%. The term "butadiene selectivity" means the mole ratio of the flow rate of butadiene in the reaction effluent obtained from said reaction step b1) to the flow rate of the mixture of ethanol and acetaldehyde consumed in said reaction step b1), expressed as a percentage. The conversion of the ethanol/acetaldehyde mixture is preferably greater than 20%, preferably greater than 25%, preferably greater than 30%. The term "conversion of the ethanol/acetaldehyde mixture" means the mole ratio between the molar flow rate of ethanol and acetaldehyde consumed in said reaction step b1), i.e. the difference in molar flow rate of the ethanol/acetaldehyde mixture between the feed and the reaction effluent obtained from said reaction step b1), and the molar flow rate of the ethanol/acetaldehyde mixture in the feed of said reaction step b1), expressed as a percentage. Preferably, at least 35%, preferably between 35% and 80%, very preferably between 40% and 80% of the acetaldehyde is converted in said reaction step b1).

Optionally, step b) of the process of the invention may also comprise a separation section for separating the reaction effluent obtained from the reaction step b1) into at least a gaseous effluent and a liquid effluent. Said separation section uses gas/liquid separation means known to those skilled in the art. The gas/liquid separator preferably used is a separator operated at a pressure of between 0.1 and 0.3 MPa, and a temperature of between 25 and 60° C. Preferably, said gaseous effluent is treated subsequent to said process according to the invention to produce a stream of purified butadiene and the liquid effluent is treated to produce notably a stream rich in unconverted ethanol and/or a stream rich in acetaldehyde. Said stream rich in unconverted ethanol may be advantageously recycled upstream of step a) for conversion of ethanol into acetaldehyde and/or upstream of step b) for conversion into butadiene, on conclusion of step a). Said stream rich in acetaldehyde may be advantageously recycled upstream of step b) and on conclusion of step a) of the process of the invention.

In accordance with the invention, said reaction-regenerative section of step b) for conversion into butadiene comprises a step b2) of regeneration, in particular of loop regeneration, in the non-operational fixed-bed reactors. At a given moment, n/2 of said fixed-bed reactors of said reaction-regenerative section are non-operational. In each reactor of said reaction-regenerative section, said step b2) is operated on conclusion of reaction step b1), for a time equal to half of the catalytic cycle time of said catalyst (Cb). For example, when the catalytic cycle time of the catalyst (b) is 10 days, the duration of the regeneration step b2) is 5 days. Said regeneration step b2) is an in situ regeneration of the catalyst (Cb) used during the second reaction step for transformation of ethanol into butadiene, i.e. used during reaction step b1) of the process according to the invention. It is known that this second reaction step (step of conversion of an ethanol/acetaldehyde mixture into butadiene) involves a plurality of chemical reactions which may be the source of many byproducts and thus of rapid fouling of the catalyst. Thus, the catalytic cycle of the catalyst (Cb), in particular based on tantalum, of this second reaction step is generally relatively short, notably less than or equal to 20 days, more particularly less than or equal to 15 days, for example equal to 10 days, and the amount of coke deposited on said catalyst at the end of the catalytic cycle is relatively large. Thus, in situ regeneration, preferably loop regeneration, of the catalyst (Cb) in the multiple reactors of step b) of the process according to the invention appears essential to ensure the continuous production of butadiene, while at the same time limiting the consumption of utilities, in particular of the inert gas, such as nitrogen, required in large amounts notably to limit the exothermicity of the burning of the coke, during the regeneration step.

In accordance with the invention, step b2) of regeneration of the catalyst (Cb) comprises, preferably consists of, four successive phases operated in the n/2 non-operational fixed-bed reactors.

First there is a stripping phase i) which starts, in a fixed-bed reactor, on conclusion of the reaction step b1). Said stripping step i) is operated at a temperature of between 300 and 400° C., preferably between 330 and 370° C., very preferably between 340° C. and 360° C., under a stream of inert gas. The inert gas is nitrogen, carbon dioxide ($CO_2$) or mixtures thereof, and preferably nitrogen. Advantageously, the flow rate of inert gas is between 0.5 and 1.5 $Nm^3/h/kg$ of catalyst and is preferably equal to 1 $Nm^3/h/kg$ of catalyst. Very preferably, this stripping phase i) lasts between 2% and 20%, preferably between 5% and 15%, of the total duration of said regeneration step b2), i.e. between 1% and 10%, preferably between 3% and 7%, of the catalytic cycle time of the catalyst (Cb) for step b) of the process according to the invention. This initial stripping phase i) is followed by a first combustion phase ii), said to be under low $O_2$ conditions, during which the soft coke is calcined. The term "soft coke" means the coke compounds deposited on the catalyst which have a relatively low degradation temperature (in particular below 400° C.), for instance compounds resulting from the oligomerization of olefins, notably C4 olefins. During the first combustion phase ii), there may also be a start of calcination of the hard coke, which groups together the hydrocarbon-based compounds with a higher degradation temperature, in particular greater than or equal to 400° C. and less than or equal to 450° C. Said first combustion phase ii) is operated under a gas stream comprising said inert gas and oxygen (in the form of $O_2$) in a content of less than or equal to 1 vol % relative to the total volume of said gas stream, preferably in a content of between 0.1 and 1 vol %, preferentially between 0.3 and 0.7 vol % relative to the total volume of said gas stream. Said first combustion phase ii) is advantageously operated at a temperature of between 300 and 450° C., preferably between 330 and 430° C., in particular at a constant temperature of between 330 and 370° C. followed by a temperature increase ramp of 10 to 30° C./h and then a phase at a constant temperature of between 390 and 430° C. Advantageously, the flow rate of said gas stream, comprising the inert gas and oxygen (in the form of $O_2$) in a content of less than or equal to 1 vol %, is between 3.5 and 5.0 $Nm^3$/h/kg of catalyst, preferably between 3.8 and 4.6 $Nm^3$/h/kg of catalyst. Very preferably, said first combustion phase ii) lasts between 5% and 40%, preferably between 10% and 30%, of the total duration of said regeneration step b2), i.e. between 2% and 20%, preferably between 5% and 15%, of the catalytic cycle time of the catalyst (Cb) for step b) of the process according to the invention.

A second combustion phase iii), said to be under high $O_2$ conditions, is performed on conclusion of the first combustion phase ii) to burn off the residual coke, i.e. the coke compounds with the highest degradation temperatures, notably greater than 450° C. Said second combustion phase iii) is operated under a gas stream comprising said inert gas and oxygen (in the form of $O_2$) in a content of greater than or equal to 2 vol % relative to the total volume of said gas stream, preferably in a content of between 2 and 20 vol %, preferentially between 2 and 10 vol %, more preferentially between 4 and 8 vol %, relative to the total volume of said gas stream. Said second combustion phase iii) is advantageously operated at a temperature of between 390 and 550° C., preferably at a constant temperature of between 390 and 430° C. followed by a temperature increase ramp of 10 to 30° C./h and then a phase at a constant temperature of between 460 and 510° C. Advantageously, the flow rate of said gas stream, comprising the inert gas and oxygen (in the form of $O_2$) in a content of greater than or equal to 2 vol %, is between 2.5 and 3.5 $Nm^3$/h/kg of catalyst, preferably between 2.7 and 3.0 $Nm^3$/h/kg of catalyst. Very preferably, said second combustion phase iii) lasts between 5% and 40%, preferably between 10% and 30%, of the total duration of said regeneration step b2), i.e. between 2% and 20%, preferably between 5% and 15%, of the catalytic cycle time of the catalyst (Cb) for step b) of the process according to the invention.

Finally, the regeneration step b2) comprises a final stripping phase iv), performed on conclusion of the second combustion phase iii), in each of said fixed-bed reactors, in particular non-operational reactors, under a stream of said inert gas, preferably of nitrogen, of carbon dioxide ($CO_2$) or mixtures thereof, and very preferably under a stream of nitrogen, advantageously at a flow rate of between 0.5 and 1.5 $Nm^3$/h/kg of catalyst, preferably equal to 1 $Nm^3$/h/kg of catalyst. Said final stripping phase iv) is advantageously operated at a temperature of between 550 and 300° C., preferably on a temperature decrease ramp of 50 to 150° C./h followed by a phase at a constant temperature of between 300 and 400° C., preferably between 330 and 370° C. Very preferably, said final stripping phase iv) lasts between 2% and 20%, preferably between 5% and 15%, of the total duration of said regeneration step, i.e. between 1% and 10%, preferably between 3% and 7%, of the catalytic cycle time of the catalyst (Cb) for step b) of the process according to the invention. Advantageously, the stripping phases i) and iv) notably make it possible to remove the residual combustion products from the reactors before and after the coke combustion.

Said phases i), ii), iii) and iv) of said regeneration step b2) are operated successively and in this order in each of said (n+n/2) fixed-bed reactors, and advantageously on conclusion of the reaction step b1).

On conclusion of the final stripping phase iv) of the regeneration step b2), the bed reactors which have undergone the regeneration step b2) are considered to be operational and reaction step b1) may advantageously be implemented in these reactors, which are said to be regenerated. Thus, in each of said (n+n/2) fixed-bed reactors of the reaction-regenerative section of the process according to the invention, the reaction step b1) and the regeneration step b2) are performed successively, advantageously cyclically. In parallel, at a given moment of the process of the invention, the reaction step b1) and the regeneration step b2) are operated simultaneously in the multi-reactor system used in the process according to the invention.

Very advantageously, said reaction-regenerative section of step b) of the process according to the invention comprises at least two regeneration loops and preferentially at least three regeneration loops, preferably two or three regeneration loops. Preferably, said reaction-regenerative section of step b) of the process according to the invention also comprises a system of lines and of valves for connecting said (n+n/2) fixed-bed reactors to the regeneration loops, to avoid circulation of the regeneration gas streams in the operational reactors and to circulate the gas streams suitable for the regeneration phases of step b2) in the non-operational reactors.

In particular, said reaction-regenerative section of step b) of the process according to the invention comprises a regeneration loop for the inert gas and at least one regeneration loop, preferably one or two regeneration loops, for the gas streams comprising oxygen. Each regeneration gas stream is recovered at the outlet of the non-operational reactors, purged and/or purified to remove the compounds resulting from the coke combustion, for instance CO, $CO_2$ or water, separated and at least partially recycled. Thus, as a function of the regeneration phase, at least a portion of an inert gas stream, very preferably a nitrogen stream, a gas stream with a low content of oxygen (i.e. an $O_2$ content of less than or equal to 1 vol % relative to the total volume of said gas stream) or a gas stream with a high content of oxygen (i.e. an $O_2$ content of greater than or equal to 2 vol % relative to the total volume of said gas stream) may be recovered, treated and recycled. Each regeneration loop preferably comprises a purge and/or a supply of corresponding gas stream.

Preferably, said reaction-regenerative section of step b) advantageously comprises an inert gas regeneration loop to recover, treat and at least partly recycle the inert gas streams leaving the reactor during the stripping phases i) and iv), and at least one regeneration loop for the gas streams comprising oxygen, preferably only one regeneration loop for the gas streams comprising oxygen, to recover, treat and at least partly recycle the gas streams leaving the reactor during the combustion phases ii) and iii). When the reaction-regenerative section comprises two oxygen regeneration loops (i.e. three regeneration loops), one of said regeneration loops for the gas streams comprising oxygen makes it possible to treat and at least partly recycle the gas stream with a low $O_2$ content (less than or equal to 1 vol % relative to the total volume of said gas stream) necessary for the first combustion phase ii) and the other makes it possible to treat and at least partly recycle the gas stream with a high $O_2$ content (greater than or equal to 2 vol % relative to the total volume of said gas stream) necessary for the second combustion phase iii), the inert gas regeneration loop making it possible, for its part, to treat and at least partly recycle the inert gas streams leaving the reactor during the stripping phases i) and iv). When the regeneration section comprises only one regeneration loop for the gas streams comprising oxygen, the inert gas regeneration loop makes it possible to treat and at least partly recycle the inert gas streams leaving the reactor during the stripping phases i) and iv) and the oxygen regeneration loop makes it possible to treat and at least partly recycle the gas streams comprising oxygen during the combustion phases ii) and iii).

Thus, the process according to the invention can ensure the continuous production of butadiene, with limited variations in the composition of the reaction effluent and thus low fluctuations in butadiene production (i.e. low fluctuations in the flow rate of butadiene produced), while at the same time limiting the consumption of utilities, in particular the consumption of inert gas such as nitrogen. The process according to the invention also affords economic savings for a process for producing butadiene from ethanol, in two reaction steps, in particular for a more global process of the type described, for example, in patent FR 3 026 100. The Figures incorporated into the present description and the examples that follow are presented as nonlimiting illustrations of the process according to the invention.

EXAMPLES

The following examples are based on simulations of processes incorporating thermodynamic data set up on experimental points.

In each of the following examples, the process described is incorporated into a more global process such as the one described in French patent FR 3 026 100. The ethanol feedstock for the global process is obtained from a renewable source and comprises more than 93% by weight of ethanol. The flow rate of feedstock feeding the global process is adjusted so as to obtain an annual production of 150 kt/year of a butadiene having a purity of between 99.5% and 100% by weight (compatible with the current use of the product), with an annual duration of functioning of the process of 8000 hours.

In the following examples, the term "variation(s) of composition" means the mean amplitude(s) of variation of the weight contents of the compounds of the reaction effluent, over the duration of functioning.

Example A1 (Not in Accordance)

In this example, the regeneration section comprises one regeneration loop per reactor.

The conversion of ethanol into acetaldehyde is performed in a multitubular reactor comprising a catalyst based on copper oxide on a silica support, at 275° C. and 0.26 MPa. The ethanol/acetaldehyde effluent, separated from the hydrogen stream at the reactor outlet, is then sent to the second reaction unit.

Figure 1:
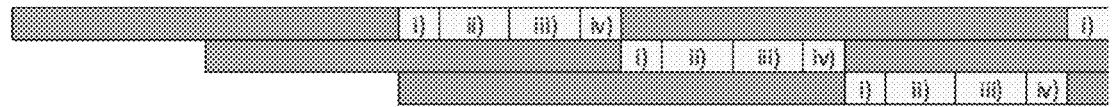
FIG. 1 shows, schematically and in a nonlimiting manner, an operating diagram of fixed-bed reactors in a system containing three fixed-bed reactors, during step b) of conversion into butadiene, a line corresponding to the functioning of a reactor, the steps in dark gray corresponding to the reaction steps b1), the steps in light gray corresponding to the various phases of the regeneration step b2): the phases i) corresponding to the stripping phases i), the phases ii) corresponding to the first combustion phases ii), the phases iii) corresponding to the second combustion phases iii) and the phases iv) corresponding to the final stripping phases iv).
Figure 2:
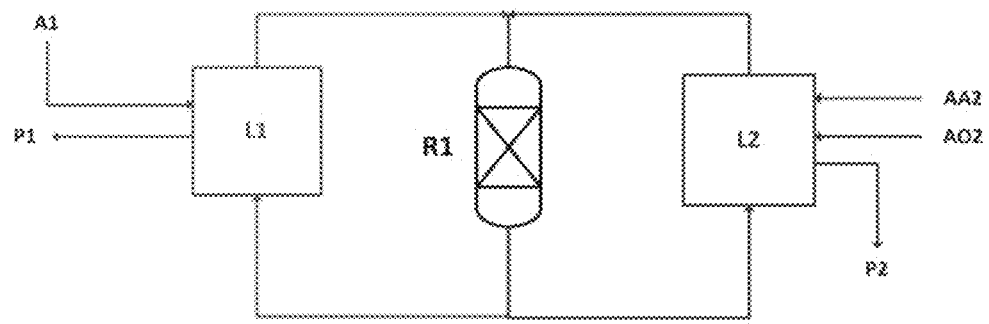
FIG. 2 shows the scheme of the regeneration step b2) in a fixed-bed reactor (R1) in non-operational mode (i.e. in a multi-reactor system comprising three fixed-bed reactors), comprising two regenerative loops, a regeneration loop (L1) for the inert gas and a regeneration loop (L2) for the gas stream comprising oxygen. Each regeneration loop (L1) and (L2) comprises a purge, (P1) and (P2), respectively. The regeneration loop (L1) for the inert gas (or stripping loop) also comprises a supply (A1) of inert gas. The regeneration loop (L2) for the gas streams comprising oxygen comprises a supply (AA2) of inert gas and a supply of dioxygen (AO2) (for example in the form of an air supply).
Figure 3:
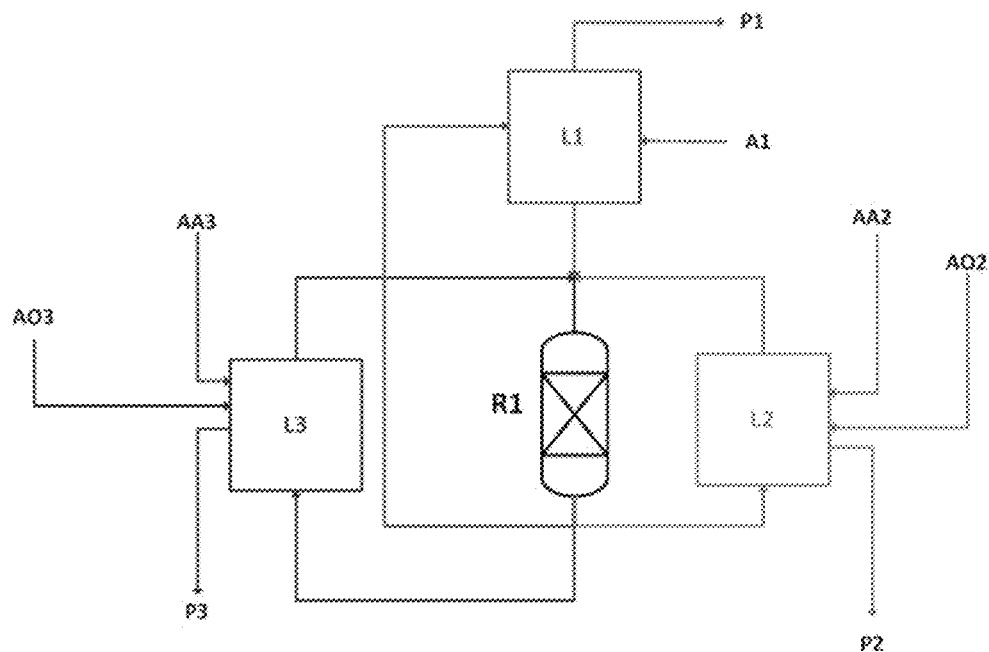
FIG. 3 shows the scheme of the regeneration step b2) in a fixed-bed reactor (R1) in non-operational mode (i.e. in a multi-reactor system comprising three fixed-bed reactors), comprising three regenerative loops, a regeneration loop (L1) for the inert gas, a regeneration loop (L2) for the gas stream with a low oxygen content and a regeneration loop (L3) for the gas stream with a high oxygen content. Each regeneration loop (L1), (L2) and (L3) comprises a purge, (P1), (P2) and (P3), respectively. The regeneration loop (L1) for the inert gas (or stripping loop) also comprises a supply (A1) of inert gas. The regeneration loop (L2) for the gas stream with a low oxygen content (or low $O_2$ loop) comprises a supply (AA2) of inert gas and a supply of dioxygen (AO2) (for example in the form of an air supply) and the regeneration loop (L3) for the gas stream with a high oxygen content (or high $O_2$ loop) also comprises a supply (AA3) of inert gas and a supply of dioxygen (AO3) (for example in the form of an air supply).

The second reaction unit comprises three radial fixed-bed reactors, each containing a fixed bed of a catalyst based on tantalum oxide on a silica-based matrix. In the second reaction unit, the conversion into butadiene is performed in the radial fixed-bed reactors, at 380° C. and 0.2 MPa and at an hourly space velocity (HSV) of 1.2 $h^{-1}$. Supplies of ethanol and of acetaldehyde, obtained from the sections for purification and separation of the unconverted ethanol and acetaldehyde streams downstream of the reaction units, are added to the ethanol/acetaldehyde effluent entering the second reaction unit, so that the total flow rate of ethanol/acetaldehyde mixture is equal to 129.7 t/h. Under these conditions, the ethanol conversion in the second reaction step is 23 mol % and the catalytic cycle of the catalyst based on tantalum oxide is 10 days. The three reactors function in parallel and sequentially as represented schematically in FIG. 1: each starts the reaction cycle with an offset of 5 days; at a given moment, two reactors are operational and one reactor is in the regeneration phase. The catalyst is regenerated in situ in each reactor under a stream of nitrogen according to the protocol presented in Table 1. The regeneration section comprises one regeneration loop per reactor.

Table 3 indicates variations of compositions in the reaction effluent. Over the duration of functioning of the process, the butadiene production varies by only 14% by weight.

Table 3 shows the consumptions of utilities for the regeneration.

Example A2 (in Accordance)

In this example, the second reaction unit comprises two regeneration loops: a nitrogen loop and a loop for the $N_2+O_2$ gas streams.

The conditions for the conversion of ethanol into acetaldehyde and for the conversion of the ethanol/acetaldehyde mixture into butadiene are the same as those of Example A1. The second reaction unit comprises three radial fixed-bed reactors comprising the same catalyst based on tantalum oxide as that described in Example A1. As for Example A1, the catalytic cycle of the catalyst based on tantalum oxide is 10 days. The three radial fixed-bed reactors function as for Example A1, in parallel and in sequence with a time offset of 5 days (cf. the scheme of FIG. 1). The regeneration of the catalyst based on tantalum oxide follows the protocol presented in Table 1. The regeneration section comprises a nitrogen loop for providing the nitrogen stream required for the regeneration, purifying it and recycling it, and an oxygen loop for ensuring the circulation, purification and recycling of the gas streams comprising nitrogen and $O_2$ at 0.5 and 6 vol % required for the regeneration for the combustion phases.

Table 2 indicates variations of compositions in the reaction effluent. Over the duration of functioning of the process, the variations in composition of the effluent are relatively low. In particular, the butadiene production varies by only 14% by weight.

Table 3 shows the consumptions of utilities, for the regeneration of the catalyst based on tantalum oxide, of all of the reactors, over the duration of functioning.

Example A3 (in Accordance)

In this example, the regeneration section comprises three regeneration loops for the three reactors: a nitrogen loop, a loop for a gas stream with a low $O_2$ content and a loop for a gas stream with a high $O_2$ content.

The conditions for the conversion of ethanol into acetaldehyde and for the conversion of the ethanol/acetaldehyde mixture into butadiene are the same as those of Example A1. As for Example A1, the catalytic cycle of the catalyst based on tantalum oxide is 10 days. The three radial fixed-bed reactors function as for Example A1, in parallel and in sequence with a time offset of 5 days. The regeneration of the catalyst based on tantalum oxide follows the protocol presented in Table 1. The regeneration section comprises:
 a nitrogen loop for providing the nitrogen stream necessary for stripping the catalyst,
 a loop for a gas stream with a low $O_2$ content for providing a gas stream comprising nitrogen and 0.5 vol %, and
 a loop for a gas stream with a low $O_2$ content for providing a gas stream comprising nitrogen and 6.0 vol % of $O_2$.

Table 2 indicates variations in composition of the reaction effluent, over the duration of functioning. The variations in composition of the effluent are relatively low. In particular, the butadiene production varies by only 14% by weight.

Table 3 shows the consumptions of utilities, for the regeneration of the catalyst based on tantalum oxide, of all of the reactors, over the duration of functioning.

TABLE 1

Regeneration protocol for Examples A1, A2 and A3

| Period | Initial T, °C. | Final T, °C. | Ramp, °C./h | vol % $O_2$ | Stage time, h |
|---|---|---|---|---|---|
| I | 350 | 350 | — | 0.0 | 12 |
| II | 350 | 350 | — | 0.5 | 30 |
| III | 350 | 410 | 20 | 0.5 | 3 |
| IV | 410 | 410 | — | 0.5 | 16.5 |
| V | 410 | 410 | — | 6.0 | 19 |
| VI | 410 | 480 | 20 | 6.0 | 3.5 |
| VII | 480 | 480 | — | 6.0 | 20 |
| VIII | 480 | 350 | 100 | 0.0 | 1.5 |
| IX | 350 | 350 | — | 0.0 | 12 |

TABLE 2

Variations of compositions in the reaction effluent for Examples A1, A2 and A3

| Component | Variation, weight % |
|---|---|
| Ethanol | 2.1 |
| Acetaldehyde | 10.7 |
| Butadiene | 13.6 |
| Diethyl ether | 10.8 |

TABLE 3

Consumptions of the utilities for the regeneration step of the processes described in Examples A1, A2 and A3

| | Example A1 | Example A2 | Example A3 |
|---|---|---|---|
| Nitrogen, Nm3/h | 6545.43 | 2147.43 | 44.90 |
| Air Instrument, Nm3/h | 1182.99 | 1162.49 | 899.05 |
| Electricity, kW | 4006.74 | 5862.55 | 5837.82 |
| Boiler water t/h | 4.46 | 8.99 | 5.76 |
| Gas fuel, kW | 4753.93 | 9314.87 | 6149.57 |

It is clearly seen that the consumption of nitrogen is very high when the regeneration section comprises one regeneration loop per reactor (Example A1 not in accordance): in particular, the nitrogen consumption is 6545.43 Nm³/h over the duration of functioning of the process. When the regeneration section comprises two or three loops for the set of three reactors as in Examples A2 and A3 in accordance, the nitrogen consumption decreases greatly: it is divided by three relative to the process comprising one loop per reactor when the regeneration section comprises two loops (nitrogen consumption equal to 2147.43 Nm³/h) and by more than 100 relative to the process comprising one loop per reactor when the regeneration section comprises three loops (nitrogen consumption equal to 44.90 Nm³/h).

Example B1 (Not in Accordance)

In this example, the multi-reactor system comprises two reactors: one reactor is in operational mode while the second is in regeneration (non-operational) mode.

All the other reaction and regeneration parameters are similar to those of Example A2.

The butadiene production leaving the production unit in this case of a system with two reactors varies by about 30% by weight.

Table 4 indicates variations of compositions in the reaction effluent.

TABLE 4

| Component | Variation, weight % |
|---|---|
| Ethanol | 4.6 |
| Acetaldehyde | 22.6 |
| Butadiene | 29.3 |
| Diethyl ether | 27.4 |

Variations of compositions in the reaction effluent

It is seen that the variations in composition of the effluent are greater at the outlet of the unit with two reactors (Example B1, Table 4) than those observed in the systems with three reactors described in Examples A1, A2 and A3 (cf. Table 2). In particular, the butadiene production in this case of a system with two reactors of Example B1 not in accordance varies by about 30% by weight, which is more than double the variations in butadiene production observed in the case of the systems with three reactors (two operational reactors+one regeneration reactor) as described in Examples A2 and A3 in accordance with the invention.

The invention claimed is:

1. A process for producing butadiene from ethanol, comprising at least the following steps:
   a) a step of converting ethanol into acetaldehyde, to produce an ethanol/acetaldehyde effluent, wherein the step of converting ethanol into acetaldehyde is carried out in at least one reaction section (A) fed with a stream comprising the ethanol and operated in the presence of a catalyst (Ca);
   b) a butadiene producing step carried out in at least one reaction-regenerative section in which are simultaneously performed a reaction step and a regeneration step in (n+n/2) fixed-bed reactors, n being an integer equal to 2 or a multiple thereof, said (n+n/2) fixed-bed reactors each comprising at least one fixed bed of a catalyst (Cb), said (n+n/2) fixed-bed reactors functioning in parallel and in sequence so that said reaction step starts in each of said reactors with a time shift equal to half of the catalytic cycle time of said catalyst (Cb), said reaction-regenerative section comprising a regeneration loop for inert gas and at least one regeneration loop for a gas stream comprising oxygen, and so that, at each instant:
   b1) said reaction step is operated in n of said fixed-bed reactors, n being as defined above, fed at least with a fraction of said ethanol/acetaldehyde effluent obtained from step a), at a temperature of between 300 and 400° C., at a pressure of between 0.1 and 1.0 MPa, for a time equal to the catalytic cycle time of said catalyst (b), to produce a reaction effluent comprising butadiene, and
   b2) said regeneration step is operated in n/2 of said fixed-bed reactors for a total time equal to half of the catalytic cycle time of said catalyst (Cb), and comprises the following four successive phases:
      i) a stripping phase operated at a temperature of between 300 and 400° C., under a stream of inert gas, said phase i) starting on conclusion of the reaction step b1); and then
      ii) a first combustion phase operated on conclusion of phase i) under a gas stream comprising said inert gas and oxygen in a content of less than or equal to 1 vol % relative to the total volume of said gas stream, at a temperature of between 300 and 450° C.; and then
      iii) a second combustion phase operated on conclusion of the first combustion phase ii) under a gas stream comprising said inert gas and oxygen in a content of greater than or equal to 2 vol % relative to the total volume of said gas stream, at a temperature of between 390 and 550° C.; and then
      iv) a final stripping phase operated at a temperature of between 550° C. and 300° C., under a stream of said inert gas.

2. The process as claimed in claim 1, in which the reaction section of step a) is operated at a temperature of between 200 and 500° C., and at a pressure of between 0.1 and 1.0.

3. The process as claimed in claim 1, in which said fixed-bed reactors used in said reaction step b1) are also fed with an additional supply of ethanol and/or a supply of acetaldehyde, the feed flow rates being such that the mole ratio between the total molar amount of ethanol relative to the total molar amount of acetaldehyde entering said fixed-bed reactors of said reaction step b1) is between 1 and 5.

4. The process as claimed in claim 1, in which the integer n is equal to 2 and said reaction-regenerative section of step b) comprises three fixed-bed reactors.

5. The process as claimed in claim 1, in which said reaction step b1) is operated at a temperature of between 300 and 360° C.

6. The process as claimed in claim 1, in which said reaction step b1) is operated at a pressure of between 0.2 and 0.4 MPa.

7. The process as claimed in claim 1, in which the catalytic cycle time of said catalyst (Cb) for the butadiene conversion step b) is greater than or equal to 1 day, and less than or equal to 20 days.

8. The process as claimed in claim 1, in which the inert gas of the regeneration step b2) is nitrogen, carbon dioxide ($CO_2$) or a mixture thereof.

9. The process as claimed in claim 1, in which said stripping phase i) is operated at a temperature of between 330 and 370° C.

10. The process as claimed in claim 1, in which the flow rate of inert gas of said stripping phase i) is between 0.5 and 1.5 $Nm^3$/h/kg of catalyst.

11. The process as claimed in claim 1, in which said first combustion phase ii) is operated under a gas stream comprising an oxygen content of between 0.1 and 1 vol % relative to the total volume of said gas stream.

12. The process as claimed in claim 1, in which said first combustion phase ii) is operated at a temperature of between 330 and 430° C.

13. The process as claimed in claim 1, in which said first combustion phase ii) is operated at a flow rate of gas stream of between 3.5 and 5.0 $Nm^3$/h/kg of catalyst.

14. The process as claimed in claim 1, in which said second combustion phase iii) is operated under a gas stream comprising an oxygen content of between 2 and 20 vol % relative to the total volume of said gas stream.

15. The process as claimed in claim 1, in which said second combustion phase iii) is operated at a constant temperature of between 390 and 430° C. followed by a temperature increase ramp of 10 to 30° C./h and then a phase at a constant temperature of between 460 and 510° C.

16. The process as claimed in claim 1, in which said second combustion phase iii) is operated at a flow rate of gas stream of between 2.5 and 3.5 $Nm^3$/h/kg of catalyst.

17. The process as claimed in claim 1, in which said final stripping phase iv) is operated on a temperature decrease ramp of 50 to 150° C./h followed by a phase at a constant temperature of between 300 and 400° C.

18. The process as claimed in claim 1, in which said final stripping phase iv) is operated under a stream of said inert gas, at a flow rate of between 0.5 and 1.5 Nm$^3$/h/kg of catalyst.

19. The process as claimed in claim 1, in which said first combustion phase ii) is operated at a constant temperature of between 330 and 370° C. followed by a temperature increase ramp of 10 to 30° C./h and then a phase at a constant temperature of between 390 and 430° C.

20. The process as claimed in claim 1, in which the reaction section of step a) is operated at a temperature of between 250 and 300° C., and at a pressure of between 0.1 and 0.3 MPa.

* * * * *